(12) United States Patent
Syed et al.

(10) Patent No.: US 11,166,885 B2
(45) Date of Patent: Nov. 9, 2021

(54) PERSONAL CARE GEL AND METHOD

(71) Applicant: Colgate-Palmolive Company, New York, NY (US)

(72) Inventors: Farrah Syed, Hamilton, NJ (US); Cheryl Kozubal, Somerset, NJ (US); Marian Holerca, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 27 days.

(21) Appl. No.: 16/334,490

(22) PCT Filed: Sep. 22, 2016

(86) PCT No.: PCT/US2016/053144
§ 371 (c)(1),
(2) Date: Mar. 19, 2019

(87) PCT Pub. No.: WO2018/056989
PCT Pub. Date: Mar. 29, 2018

(65) Prior Publication Data
US 2019/0209442 A1    Jul. 11, 2019

(51) Int. Cl.
| | | |
|---|---|---|
| *A61K 8/04* | (2006.01) | |
| *A61K 8/34* | (2006.01) | |
| *A61K 8/39* | (2006.01) | |
| *A61K 8/44* | (2006.01) | |
| *A61K 8/81* | (2006.01) | |
| *A61K 8/86* | (2006.01) | |
| *A61Q 19/00* | (2006.01) | |
| *A61K 8/37* | (2006.01) | |
| *A61K 8/92* | (2006.01) | |
| *A61Q 17/04* | (2006.01) | |
| *A61K 8/33* | (2006.01) | |

(52) U.S. Cl.
CPC .............. *A61K 8/042* (2013.01); *A61K 8/33* (2013.01); *A61K 8/345* (2013.01); *A61K 8/375* (2013.01); *A61K 8/39* (2013.01); *A61K 8/44* (2013.01); *A61K 8/8147* (2013.01); *A61K 8/86* (2013.01); *A61K 8/922* (2013.01); *A61Q 17/04* (2013.01); *A61Q 19/00* (2013.01); *A61Q 19/007* (2013.01)

(58) Field of Classification Search
CPC ...................................................... A61K 8/042
See application file for complete search history.

(56) References Cited

U.S. PATENT DOCUMENTS

| | | | |
|---|---|---|---|
| 5,156,845 A | 10/1992 | Grodberg | |
| 5,849,273 A | 12/1998 | Bonda et al. | |
| 6,156,293 A | 12/2000 | Jutila et al. | |
| 7,740,878 B2 | 6/2010 | Craig | |
| 7,763,595 B2 | 7/2010 | Kambayashi et al. | |
| 8,540,970 B2 | 9/2013 | Rodriguez-Vilaboa | |
| 8,697,147 B2 | 4/2014 | Le Fur et al. | |
| 8,697,750 B2 | 4/2014 | Omura et al. | |
| 8,747,827 B2 | 6/2014 | Chihiro | |
| 8,758,785 B2 | 6/2014 | Miyamoto et al. | |
| 9,155,915 B2 | 10/2015 | Kunin | |
| 9,289,498 B2 | 3/2016 | Matsuo et al. | |
| 2004/0028634 A1* | 2/2004 | Tanaka | A61K 8/891 424/70.12 |
| 2004/0121020 A1* | 6/2004 | Moloney | A61K 2300/00 424/539 |
| 2015/0051169 A1 | 2/2015 | Gupta | |
| 2016/0206523 A1 | 7/2016 | Obias et al. | |

FOREIGN PATENT DOCUMENTS

| | | | |
|---|---|---|---|
| CN | 1486173 | | 3/2004 |
| CN | 1883449 | | 12/2006 |
| CN | 101182299 | | 5/2008 |
| CN | 101547677 | | 9/2009 |
| CN | 101700218 B | | 5/2010 |
| CN | 103462843 | | 12/2013 |
| CN | 103492029 | | 1/2014 |
| CN | 105663605 | | 6/2016 |
| CN | 105722497 | | 6/2016 |
| EP | 2628487 | * | 8/2013 |
| JP | 2010064986 A | | 3/2010 |
| KR | 20140092425 A | | 7/2014 |
| RU | 2244540 | | 1/2005 |

(Continued)

OTHER PUBLICATIONS

International Search Report and Written Opinion of the International Searching Authority in International Application No. PCT/US2016/053144, dated Dec. 8, 2016.

(Continued)

*Primary Examiner* — Nicole P Babson

(57) ABSTRACT

A moisturizing gel composition is disclosed containing 4 wt. % to 12 wt. % of a humectant selected from trimethylglycine, propylene glycol, glycerin and combinations thereof; 1 wt. % to 6 wt. % of a skin feel agent selected from PEG-14M, polyglyceryl-3-laurate, ppg-3 isostearyl methyl ether, PEG60 almond glyceride, and combinations thereof; 0.25 wt. % to 1 wt. % of a skin conditioning agent selected from shea oil and triterpenesters; 0.2 wt. % to 2 wt. % of a structure increasing polymer selected from carbomers, acrylate polymers, acrylate copolymers and combinations thereof; and a cosmetically acceptable aqueous carrier; wherein, the composition has a pH of 4 to 7. A method to produce the composition at low temperature is further disclosed.

9 Claims, 1 Drawing Sheet

(56) References Cited

FOREIGN PATENT DOCUMENTS

| WO | 1993/024101 | 12/1993 |
|----|-------------|---------|
| WO | 1999/049841 | 10/1999 |
| WO | 2007/078856 | 7/2007 |
| WO | 2015/071298 | 5/2015 |

OTHER PUBLICATIONS

Kemin Industries, Inc., 2016, "Cold Process Lotion with Lysofix™", Formulation: KPC/PD11003.18, Kemin Formulations, [Obtained Online], Date Accessed: Aug. 23, 2016, 1 page, https://www.kemin.com/images/files/Cold_Process_Emulsification.pdf.

Making Skin Care Naturally, 2016, "Another no heat, quick lotion/moisturiser using cold process technology", Making Skin Care, Dec. 18, 2013, [Obtained Online], Date Accessed: Aug. 23, 2016, 3 pages, http://www.makingskincare.com/cold-process-lotion/.

Cholewa, "Effects of Betaine on body composition, performance, homocysteine thiolactone," Journal of International Society of Sports Nutrition, Dec. 31, 2013, pp. 1-12.

Anonymous, 2008, Detergent & Cosmetic, vol. 31, No. 3, Mar. 2008.

\* cited by examiner

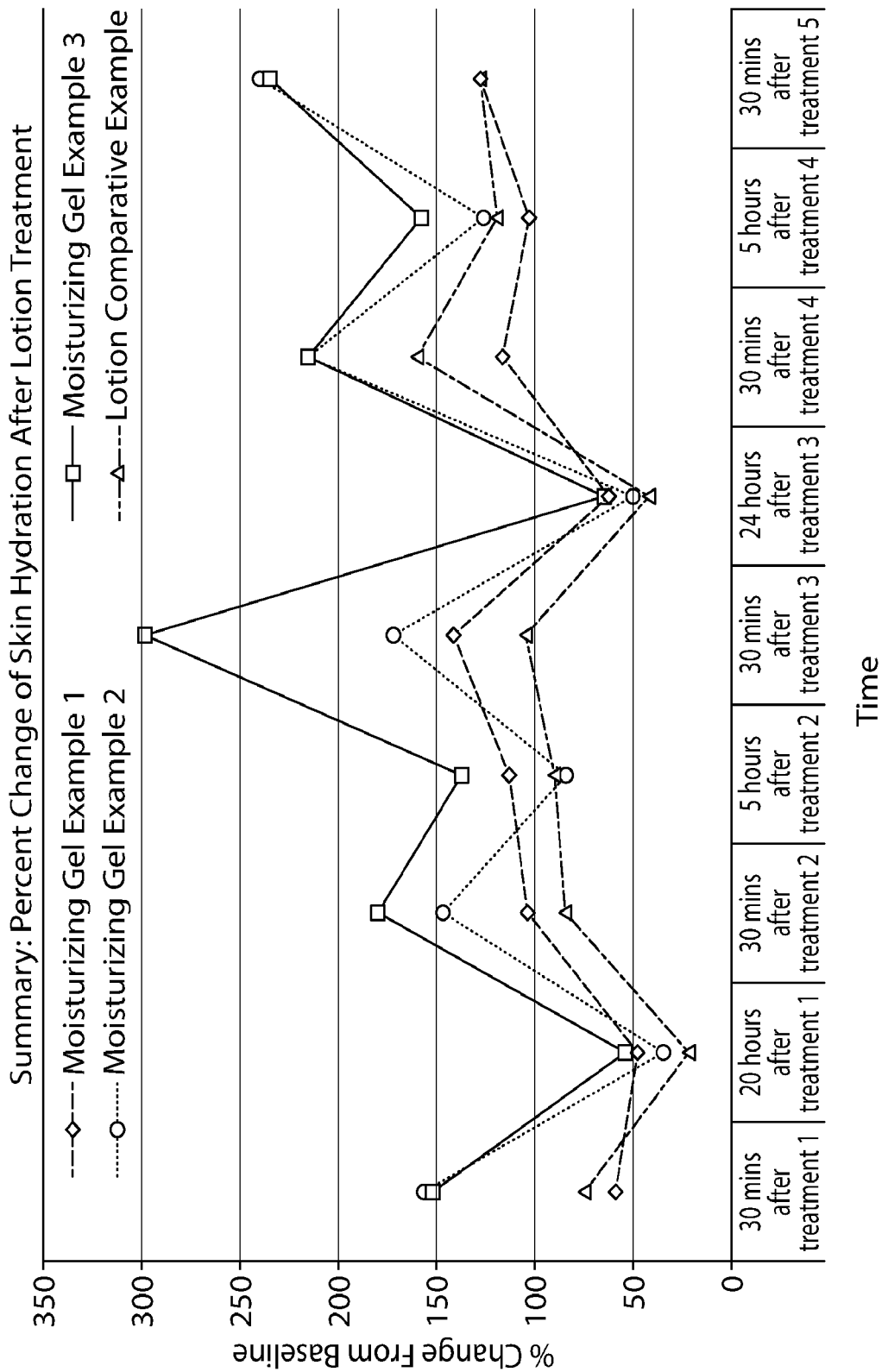

PERSONAL CARE GEL AND METHOD

BACKGROUND

Skin is composed of three superposed layers that are, from surface to body depth, epidermis, dermis and hypodermis. The epidermis can be divided, according to morphological and histological criteria, into four layers, from the deepest to the outermost: the basal lamina and the spinosal layer (which form the deep epidermis), and the granular layer (superficial epidermis) and the corneal layer (or stratum corneum). The epidermis is in contact with the external environment. One of the roles of the epidermis is to protect the organism from dehydration, as well as chemical, mechanical and biological exterior aggressions.

The dermis is an irrigated connective tissue mostly composed of fibroblasts and of an extracellular matrix made of muccopolysaccharides and of macromolecules such as collagen, elastin and fibronectin fibers. It assumes a nourishing and support function with regard to the epidermis.

Skin is known to have a tendency to dry due to environmental, psychological and hormonal factors. It is important that skin be well moisturized to prevent dry skin, including symptoms of redness, itchiness, irritation, dry patches, peeling, cracking and/or swelling. Similarly, dehydrated skin results in tightening of the skin, and/or the loss of flexibility and elasticity. Skin may become rough, even scaly.

Moisturizing products, such as moisturizing lotions, currently exist to counteract these drying effects. Moisturizing lotions are typically oil-in-water emulsions prepared by blending ingredients at a high temperature. Moisturizing lotions require the use of surfactants to maintain a stable composition at ambient temperatures. A need exists to provide consumers with new or non-traditional moisturizing options, especially ones which are more environmentally sustainable, such as through a reduced requirement for energy input during manufacture.

BRIEF SUMMARY

In an embodiment, a moisturizing gel composition is disclosed containing 1 wt. % to 12 wt. % of humectant selected from trimethylglycine, propylene glycol, glycerin and combinations thereof; 1 wt. % to 6 wt. % of skin feel agent selected from PEG-14M, polyglyceryl-3-laurate, ppg-3 isostearyl methyl ether, PEG60 almond glyceride, and combinations thereof; 0.25 wt. % to 1 wt. % of skin conditioning agent selected from shea oil and triterpenesters; 0.2 wt. % to 2 wt. % of structure increasing polymer selected from carbomers, acrylate polymers, acrylate copolymers and combinations thereof; and cosmetically acceptable aqueous carrier; wherein, the composition has a pH of 4 to 7.

In another embodiment, a moisturizing gel composition is provided containing: 0.2 wt. % to 2 wt. % Carbopol Ultrez 30, 1 wt. % to 6 wt. % trimethylglycine, 0.1 wt. % to 1 wt. % propylene glycol, 2 wt. % to 6 wt. % glycerin, 0.1 wt. % to 0.8 wt. % PEG-14M, 0.25 wt. % to 1.5 wt. % polyglyceryl-3-laurate, 0.25 wt. % to 1.5 wt. %, ppg-3 isostearyl methyl ether, 0 wt. % to 2 wt. % PEG60 almond glyceride, 0.25% wt. % to 1 wt. % Shea oil, 0.25 wt. % to 3 wt. % preservative, and 70 wt. % to 96 wt. % water, wherein, the pH of the composition is 4 to 7 and the viscosity is adjustable and can range from 5,000 cps to 300,000 cps (Brookfield viscometer).

In another embodiment, a process is provided for preparing a moisturizing gel composition comprising combining at ambient temperature ranging from 15° C. to 35° C., without the need for external heating, humectant selected from trimethylglycine, propylene glycol, glycerin and combinations thereof; skin feel agent selected from PEG-14M, polyglyceryl-3-laurate, ppg-3 isostearyl methyl ether, PEG60 almond glyceride, and combinations thereof; skin conditioning agent selected from triterpene esters (e.g. shea oil), structure increasing polymer selected from carbomers, acrylate polymers, acrylate copolymers and combinations thereof; and cosmetically acceptable carrier; blending the ingredients, and; adding a basic composition to activate thickening of the composition and provide a pH of 4 to 7, and viscosity of 5,000 cps to 300,000 cps (Brookfield viscometer).

In a further embodiment, a method of providing positive effect on skin is provided through applying a moisturizing composition according to claim 1 to skin, wherein the positive effect on skin is improved skin dryness, improved skin softness, improved skin softness, or improved skin greasiness.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 presents a graph of the results of the testing of the data for the three moisturizing gels according to the invention, and an oil-in-water emulsion-based lotion as a comparative example.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention is a non-traditional moisturizing gel composition that provides moisturization similar to a traditional oil-in-water emulsion lotion. In addition, the gel of the invention provides more eco-friendly moisturization as it can be produced by a cold process which is typically not possible with traditional oil-in-water emulsion lotions.

In an embodiment, the composition contains trimethylglycine and glycerin for moisturization in combination with additional humectants and skin feel agents including PEG-14M, Butyrospermum Parkii (Shea) Oil, Polyglyceryl-3 Laurate, PPG-3 Isostearyl Methyl Ether, Propylene Glycol and PEG-60 Almond Glycerides. The Polyglyceryl-3 Laurate and PPG-3 Isostearyl Methyl Ether were added to enhance the skin feel attributes, particularly to minimize tackiness of the formulation and improve application. The formulation is water based and Carbomer provides viscosity adjustment.

The compositions of the present invention can comprise one or more thickening agents. In one embodiment, a thickening agent is present at a level of from about 0.05% to about 10%, preferably from about 0.1% to about 5%, and more preferably from about 0.25% to about 4%, by weight of the composition. Non-limiting classes of thickening agents include those selected from the following:

Carboxylic Acid Polymers. These polymers are cross-linked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. Nos. 5,087,445, 4,509,949, 2,798,053, and in CTFA International Cosmetic Ingredient Dictionary, Tenth Edition, 2004. Examples of commercially available carboxylic acid polymers useful herein include the carbomers, which are homopolymers of acrylic acid cross-linked with allyl ethers of sucrose or pentaerythritol. The carbomers are available as the Carbopol 900 series from B.F. Goodrich (e.g., Carbopol 954). In addition, other suitable carboxylic acid polymeric agents include Ultrez 10, Ultrez 20, and Ultrez 30 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol 1342, Carbopol 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

Crosslinked Polyacrylate Polymers. The compositions of the present invention can optionally contain crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. Nos. 5,100,660, 4,849,484, 4,835,206, 4,628,078, 4,599,379 and EP 228,868.

Polyacrylamide Polymers. The compositions of the present invention can optionally contain polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the Tradename Sepigel 305 from Seppic Corporation. Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel from United Guardian. These gels have moisturizing, viscosifying, stabilizing properties and may be used in concentration ranges between 1 and 99%, most advantageously between 5 and 15%.

Polysaccharides. A wide variety of polysaccharides can be useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol CS Plus from Aqualon Corporation. Other useful polysaccharides include scleroglucans comprising a linear chain of (1-3) linked glucose units with a (1-6) linked glucose every three units, a commercially available example of which is Clearogel CS11 from Michel Mercier Products Inc.

Gums. Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

In embodiments, the composition contains a structure increasing polymer, such as acrylate polymers and acrylate copolymers. In an embodiment, the structure increasing polymer is a homopolymer of acrylic acid which is cross-linked, for example with allyl ether of pentaerythritol, allyl ether of sucrose, or allyl ether of propylene, such as the commercially available Carbomer polymers.

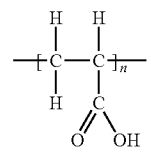

In embodiments, the polymer is present in an amount from about 0.1 wt. % to 5 wt. %, or 0.2 wt. % to 2 wt. %, or 0.2 wt. % to 1 wt. %, or 0.3 wt. % to 0.8 wt. %.

The compositions of the present invention can contain a safe and effective amount of a conditioning agent selected from, for example, humectants, moisturizers, and skin conditioners. A variety of these materials can be employed and in one embodiment can be present at a level of from about 0.01% to about 20%, more preferably from about 0.1% to about 10%, and still more preferably from about 0.5% to about 7%, by weight of the composition. These materials can include, but are not limited to, guanidine, urea, glycolic acid, glycolate salts (e.g. ammonium and quaternary alkyl ammonium), salicylic acid, lactic acid, lactate salts (e.g., ammonium and quaternary alkyl ammonium), aloe vera in any of its variety of forms (e.g., aloe vera gel), polyhydroxy alcohols such as sorbitol, mannitol, xylitol, erythritol, glycerol, hexanetriol, butanetriol, propylene glycol, butylene glycol, hexylene glycol and the like, polyethylene glycols, sugars (e.g., melibiose), starches, sugar and starch derivatives (e.g., alkoxylated glucose, fructose, glucosamine), hyaluronic acid, lactamide monoethanolamine, acetamide monoethanolamine, panthenol, allantoin, petroleum and mixtures thereof. Also useful herein are the propoxylated glycerols described in U.S. Pat. No. 4,976,953.

Also useful are various C1-C30 monoesters and polyesters of sugars and related materials. These esters are derived from a sugar or polyol moiety and one or more carboxylic acid moieties. Preferably, the conditioning agent is selected from urea, guanidine, sucrose polyester, panthenol, dexpanthenol, allantoin, glycerol, and combinations thereof.

Cationic, Anionic and Amphoteric Polymers. The compositions of the present invention can comprise polymers which may be homopolymers, copolymers, terpolymers, etc. For convenience in describing the polymers hereof, monomeric units present in the polymers may be referred to as the monomers from which they can be derived. The monomers can be ionic (e.g., anionic, cationic, amphoteric, zwitterionic) or nonionic When included, concentrations of the cationic polymer in the composition can typically range from about 0.05% to about 3%, preferably from about 0.075% to about 2.0%, more preferably from about 0.1% to about 1.0.

Cationic Polymers. Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate. Non limiting examples of such polymers are described in the CTFA. Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone. Examples of cationic monomers include monomers derived from acrylic acid or methacrylic acid, and a quaternarized epihalohydrin product of a trialkylamine having 1 to 5 carbon atoms in the alkyl such as (meth)acryloxypropyltrimethyl ammonium chloride and (meth)acryloxypropyltriethylammonium bromide; amine derivatives of methacrylic acid or amine derivatives of methacrylamide derived from methacrylic acid or methacrylamide and a dialkylalkanolamine having C1-C6 alkyl groups such as dimethylaminoethyl (meth)acrylate, diethylaminoethyl (meth)acrylate, dimethylaminopropyl (meth)acrylate, or dimethylaminopropyl (meth)acrylamide.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47). Preferred cationic substituted monomers are the cationic substituted dialkylaminoalkyl acrylamides, dialkylaminoalkyl methacrylamides, and combinations thereof. A non-limiting example is polymethyacrylamidopropyl trimonium chloride, available under the trade name Polycare 133, from Rhone-Poulenc.

Other suitable cationic polymers for use in the composition include polysaccharide polymers, such as cationic cellulose derivatives and cationic starch derivatives. Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

Anionic Polymers. Examples of anionic polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride, acrylic copolymers and terpolymers containing acrylic acid or methacrylic acid. Examples of anionic monomers include unsaturated carboxylic acid monomers such as acrylic acid, methacrylic acid, maleic acid, maleic acid half ester, itaconic acid, fumeric acid, and crotonic acid; half esters of an unsaturated polybasic acid anhydride such as succinic anhydride, phthalic anhydride or the like with a hydroxyl group-containing acrylate and/or methacrylate such as hydroxyethyl acrylate and, hydroxyethyl methacrylate, hydroxypropyl acrylate and the like; monomers having a sulfonic acid group such as styrenesulfonic acid, sulfoethyl acrylate and methacrylate, and the like; and monomers having a phosphoric acid group such as acid phosphooxyethyl acrylate and methacrylate, 3-chloro-2-acid phosphooxypropyl acrylate and methacrylate, and the like.

Amphoteric Monomers. Examples of the amphoteric monomers include zwitterionized derivatives of the aforementioned amine derivatives of (meth)acrylic acids or the amine derivatives of (meth)acrylamide such as dimethylaminoethyl(meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth)acrylic acid or (meth)acrylamide, as discussed above, modified with propanesultone.

Nonionic Polymers. The compositions herein can comprise nonionic polymers.

For instance, polyalkylene glycols having a molecular weight of more than about 1000 can be used. Preferred polyethylene glycol polymers can include PEG-2M (also known as Polyox WSR N-10, which is available from Union Carbide and as PEG-2,000); PEG-5M (also known as Polyox WS N-35 and Polyox WSR N-80, available from Union Carbide and as PEG-5,000 and Polyethylene Glycol 300,000); PEG-7M (also known as Polyox WSR N-750 available from Union Carbide); PEG-9M (also known as Polyox WSR N-3333 available from Union Carbide); and PEG-14 M (also known as Polyox WSR N-3000 available from Union Carbide).

Examples of nonionic monomers are acrylic or methacrylic acid esters of C1-C24 alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, styrene, chlorostyrene, vinyl esters such as vinyl acetate, vinyl chloride, vinylidene chloride, acrylonitrile, alpha-methylstyrene, t-butylstyrene, butadiene, cyclohexadiene, ethylene, propylene, vinyl toluene, alkoxyalkyl(meth)acrylate, methoxy ethyl(meth)acrylate, butoxyethyl(meth)acrylate, allyl acrylate, allyl methacrylate, cyclohexyl acrylate and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl(meth)acrylate, n-butyl methacrylate, isobutyl methacrylate, 2-ethylhexyl methacrylate, methyl methacrylate, t-butylacrylate, t-butylmethacrylate, and mixtures thereof.

The compositions of the present invention may contain a humectant. Humectants, when used herein, are preferably used at levels of from about 0.1% to about 20%, more preferably from about 0.5% to about 5%. Humectants can be selected from the group consisting of polyhydric alcohols, water soluble alkoxylated nonionic polymers, and mixtures thereof. Polyhydric alcohols useful herein include polyhydroxy alcohols aforementioned and glycerin, hexylene glycol, ethoxylated glucose, 1,2-hexane diol, dipropylene glycol, trehalose, diglycerin, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof. Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

In embodiments, the composition includes humectant, such as trimethylglycine, or betaine, which is the zwitterion (inner salt) that conforms to the formula:

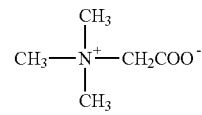

In an embodiment, the humectant is a natural product, such as tego natural betaine monohydrate. In an embodiment, betaine also includes sultaines. In other embodiments, the humectants include silicone oils or caprylyl glycol. In embodiments, the betaine is present in an amount from about 1 wt. % to 6 wt. %, or 1.5 wt. % to 4 wt. %, or 1.7 wt. % to 2.5 wt. %.

In an embodiment, the composition comprises a humectant, such as propylene glycol, which is an aliphatic alcohol that conforms generally to the formula:

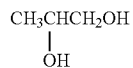

In embodiments, propylene glycol is present in an amount from about 0.01 wt. % to 1 wt. %, or 0.05 wt. % to 0.5 wt. %, or 0.07 wt. % to 0.3 wt. %.

In an embodiment, the composition contains glycerin as a humectant. Glycerin is the polyhydric alcohol that conforms generally to the formula:

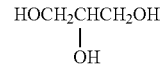

In embodiments, glycerin is present in an amount from about 2 wt. % to 6 wt. %, or 2 wt. % to 5 wt. %, or 3 wt. % to 5 wt. %.

Viscosity Increasing Agent. The composition comprises a skin feel additive, or viscosity increasing agent, such as WSR-N-60K or PEG-14M, which is a polymer of ethylene oxide that conforms generally to the formula:

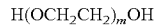

where n has an average value of 14000. In embodiments, the skin feel additive is present in an amount from about 0.01 wt. % to 1 wt. %, or 0.05 wt. % to 0.5 wt. %, or 0.07 wt. % to 0.3 wt. %.

Organic Conditioning Oils. Compositions of the present invention may also comprise organic conditioning oil. In one embodiment, from about 0.05% to about 20%, preferably from about 0.08% to about 1.5%, more preferably from about 0.1% to about 1%, of at least one organic conditioning oil is included as a conditioning agent, either alone or in combination with other conditioning agents, such as the silicones (described herein).

Hydrocarbon Oils. Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about C12 to about C19. Branched chain hydrocarbon oils, including hydrocarbon polymers, typically will contain more than 19 carbon atoms. Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation, hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation.

Polyolefins. Organic conditioning oils for use in the compositions of the present invention can also include liquid polyolefins, more preferably liquid poly-.alpha.-olefins, more preferably hydrogenated liquid poly-.alpha.-olefins. Polyolefins for use herein are prepared by polymerization of C4 to about C14 olefenic monomers, preferably from about C6 to about C12. Preferred non-limiting examples of olefenic monomers for use in preparing the polyolefin liquids herein include ethylene, propylene, 1-butene, 1-pentene, 1-hexene to 1-hexadecenes, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents.

Fatty Esters. Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.). Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, dihexyldecyl adipate, lauryl lactate, myristyl lactate, cetyl lactate, oleyl stearate, oleyl oleate, oleyl myristate, lauryl acetate, cetyl propionate, and oleyl adipate. Other fatty esters suitable for use in the compositions of the present invention are mono-carboxylic acid esters of the general formula R'COOR, wherein R' and R are alkyl or alkenyl radicals, and the sum of carbon atoms in R' and R is at least 10, preferably at least 22. Still other fatty esters suitable for use in the compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol di stearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Additional fatty esters suitable for use in the compositions of the present invention are water insoluble synthetic fatty esters. Specific non-limiting examples of suitable synthetic fatty esters for use in the compositions of the present invention include: P-43 ($C_8$-$C_{10}$ triester of trimethylolpropane), MCP-684 (tetraester of 3,3 diethanol-1,5 pentadiol), MCP 121 ($C_8$-$C_{10}$ diester of adipic acid), all of which are available from Mobil Chemical Company. In an embodiment, the composition contains ingredients known as emollients and skin feel modifiers. A wide range of skin feel modifiers can be used, such as Glyceryl Esters and Derivatives (Excluding fats and oils); Alkoxylated Alcohols (Limited to alkoxylation products of alcohols); Ethers (Excluding alkoxylated derivatives). In an embodiment, the skin feel modifiers are selected from polyglyceryl-3 laurate, PPG-3 isostearyl methyl ether, and PEG-60 almond glycerides.

Polyglyceryl-3 Laurate is the ester of lauric acid and Polyglycerin-3, commercially available as Hydramol TGL Ester.

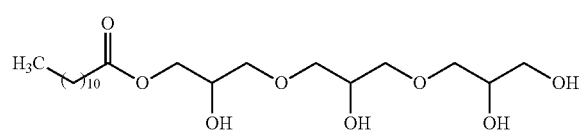

In embodiments, Polyglyceryl-3 Laurate is present in an amount from about 0.01 wt. % to 1 wt. %, or 0.05 wt. % to 0.5 wt. %, or 0.07 wt. % to 0.3 wt. %.

PPG-3 Isostearyl Methyl Ether is the methyl ether of the polyoxypropylene derivative of isostearyl alcohol containing an average of 3 moles of propylene oxide, commercially available as Arlamol LST.

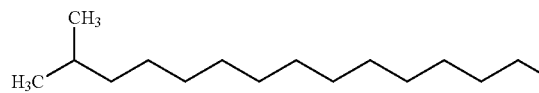

In embodiments, PPG-3 Isostearyl Methyl Ether is present in an amount from about 0.25 wt. % to 1.5 wt. %, or 0.4 wt. % to 1.2 wt. %, or 0.5 wt. % to 1 wt. %.

PEG-60 Almond Glyceride is a polyethylene glycol derivative of the mono- and diglycerides from almond oil with an average of 60 moles of ethylene oxide.

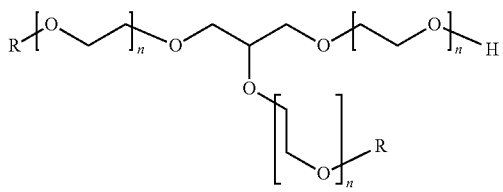

wherein R is hydrogen or the fatty acid residues from almond oil, where at least one R is a fatty acid, and the sum of all cases of n is 60. In embodiments, PEG-60 Almond Glyceride is present in an amount from about 0 wt. % to 2 wt. %, or 0.2 wt. % to 1 wt. %, or 0.3 wt. % to 0.7 wt. %.

In embodiments, the composition contains a skin conditioning agent. In embodiments, the composition contains Butyrospermum Parkii (Shea) Oil, an occlusive skin conditioning agent, in an amount from about 0.25 wt. % to 1 wt. %, or 0.3 wt. % to 0.8 wt. %, or 0.4 wt. % to 0.6 wt. %.

Dermatologically Acceptable Carrier—In an embodiment, the topical compositions of the present invention can also comprise a dermatologically acceptable carrier for the composition. In one embodiment, the carrier is present at a level of from about 50% to about 99.99%, preferably from about 60% to about 99.9%, more preferably from about 70% to about 98%, and even more preferably from about 80% to about 95%, by weight of the composition. The carrier can be in a wide variety of forms. Non-limiting examples include simple solutions (water or oil based). The compositions can therefore comprise an aqueous carrier, which is typically present at a level of from about 20% to about 95%, preferably from about 60% to about 85%. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components. In an embodiment the carrier is demineralized water.

Preservative. In an embodiment, the preservative is selected from benzalkonium chloride; benzethonium chloride, 5-bromo-5-nitro-1,3-dioxane; 2-bromo-2-nitropropane-1,3-diol; alkyl trimethyl ammonium bromide; N-(hydroxymethyl)-N-(1,3-dihydroxy methyl-2,5-dioxo-4-imidaxolidinyl-N-(hydroxy methyl)urea; 1-3-dimethyol-5, 5-dimethyl hydantoin; formaldehyde; iodopropynl butyl carbamate, butyl paraben; ethyl paraben; methyl paraben; propyl paraben, mixture of methyl isothiazolinone/methylchloroisothiazolinone in a 1:3 wt. ratio; mixture of phenoxyethanol/butyl paraben/methyl paraben/propylparaben; 2-phenoxyethanol; tri s-hydroxyethyl-hexahydrotriazine; methylisothiazolinone; 5-chloro-2-methyl-4-isothiazolin-3-one; 1,2-dibromo-2,4-dicyanobutane; 1-(3-chloroalkyl)-3,5, 7-triaza-azoniaadamantane chloride; organic acids, lactic acid, or citric acid and combinations thereof. In an embodiment, the preservative comprises sorbitan caprylate, propanediol, and benzoic acid, available commercially as Nipaguard SCE. In embodiments, preservative is present in an amount from about 0.25 wt. % to 3 wt. %, or 0.3 wt. % to 2 wt. %, or 0.3 wt. % to 0.7 wt. %.

The CTFA Cosmetic Ingredient Handbook, Tenth Edition (published by the Cosmetic, Toiletry, and Fragrance Association, Inc., Washington, D.C.) (2004) describes a non-limited wide variety of cosmetic and pharmaceutical ingredients usually used in the skin care industry that can be used as additional ingredients in the compositions of the present invention. Examples of these ingredient classes include, but are not limited to: healing agents, skin anti-aging agents, skin moisturizing agents, anti-wrinkle agents, anti-atrophy agents, skin smoothing agents, antibacterial agents, antifungal agents, pesticides anti parasitic agents, antimicrobial agents, anti-inflammatory agents, anti-pruriginous agents, external anesthetic agents, antiviral agents, keratolytic agents, free radicals scavengers, antiseborrheic agents, anti-dandruff agents, the agents modulating the differentiation, proliferation or pigmentation of the skin and agents accelerating penetration, desquamating agents, depigmenting or propigmenting agents, antiglycation agents, tightening agents, agents stimulating the synthesis of dermal or epidermal macromolecules and/or preventing their degradation; agents stimulating the proliferation of fibroblasts and/or keratinocytes or stimulating the differentiation of keratinocytes; muscle relaxants; antipollution and/or anti-free radical agents; slimming agents, anticellulite agents, agents acting on the microcirculation; agents acting on the energy metabolism of the cells; cleaning agents, hair conditioning agents, hair styling agents, hair growth promoters, sunscreen and/or sunblock compounds, make-up agents, detergents, pharmaceutical drugs, emulsifiers, emollients, antiseptic agents, deodorant actives, dermatologically acceptable carriers, surfactants, abrasives, absorbents, aesthetic components such as fragrances, colorings/colorants, essential oils, skin sensates, cosmetic astringents, anti-acne agents, anti-caking agents, anti foaming agents, antioxidants, binders, biological additives, enzymes, enzymatic inhibitors, enzyme-inducing agents, coenzymes, plant extracts, plant derivatives, plant tissue extracts, plant seed extracts, plant oils, botanicals, botanical extracts, ceramides, peptides, buffering agents, bulking agents, chelating agents, chemical additives, colorants, cosmetic biocides, denaturants, drug astringents, external analgesics, film formers or materials, e.g., polymers, for aiding the film-forming properties and substantivity of the composition, quaternary derivatives, agents increasing the substantivity, opacifying agents, pH adjusters, propellants, reducing agents, sequestrants, skin bleaching and lightening agents, skin tanning agents, skin-conditioning agents (e.g., humectants, including miscellaneous and occlusive), skin soothing and/or healing agents and derivatives, skin treating agents, thickeners, and vitamins and derivatives thereof, peeling agents, moisturizing agents, curative agents, lignans, preservatives, UV absorbers, a cytotoxic, an antineoplastic agent, a fat-soluble active, suspending agents, viscosity modifiers, dyes, nonvolatile solvents, diluents, pearlescent aids, foam boosters, a vaccine, and their mixture.

In embodiments, said additional ingredient is selected from the group consisting of sugar amines, glucosamine, D-glucosamine, N-acetyl glucosamine, N-acetyl-D-glucosamine, mannosamine, N-acetyl mannosamine, galactosamine, N-acetyl galactosamine, vitamin B3 and its derivatives, niacinamide, sodium dehydroacetate, dehydroacetic acid and its salts, phytosterols, salicylic acid compounds, hexamidines, dialkanoyl hydroxyproline compounds, soy extracts and derivatives, equol, isoflavones, flavonoids, phytantriol, farnesol, geraniol, peptides and their derivatives, di-, tri-, tetra-, penta-, and hexapeptides and their derivatives, lys-thr-thr-lys-ser, palmitoyl-ly s-thr-thr-lys-ser, carnosine, N-acyl amino acid compounds, retinoids, retinyl propionate, retinol, retinyl palmitate, retinyl acetate, retinal, retinoic acid, water-soluble vitamins, ascorbates, vitamin C, ascorbic acid, ascorbyl glucoside, ascorbyl palmitate, magnesium ascorbyl phosphate, sodium ascorbyl phosphate, vitamins their salts and derivatives, provitamins and their salts and derivatives, ethyl panthenol, vitamin B, vitamin B derivatives, vitamin B1, vitamin B2, vitamin B6, vitamin B12, vitamin K, vitamin K derivatives, pantothenic acid and its derivatives, pantothenyl ethyl ether, panthenol and its derivatives, dexpanthenol, biotin, amino acids and their salts and derivatives, water soluble amino acids, asparagine, alanine, indole, glutamic acid, water insoluble vitamins, vitamin A, vitamin E, vitamin F, vitamin D, mono-,di-, and tri-terpenoids, beta-ionol, cedrol, and their derivatives, water insoluble amino acids, tyrosine, tryptamine, butylated hydroxytoluene, butylated hydroxyanisole, allantoin, tocopherol nicotinate, tocopherol, tocopherol esters, palmitoyl-gly-his-lys, phytosterol, hydroxy acids, glycolic acid, lactic acid, lactobionic acid, keto acids, pyruvic acid, phytic acid, lysophosphatidic acid, stilbenes, cinnamates, resveratrol, kinetin, zeatin, dimethylaminoethanol, natural peptides, soy peptides, salts of sugar acids, Mn gluconate, Zn gluconate, particulate materials, pigment materials, natural colors, piroctone olamine, 3,4,4'-trichlorocarbanilide, triclocarban, zinc pyrithione, hydroquinone, kojic acid, ascorbic acid, magnesium ascorbyl phosphate, ascorbyl glucoside, pyridoxine, aloe vera, terpene alcohols, allantoin, bisabolol, dipotassium glycyrrhizinate, glycerol acid, sorbitol acid, pentaerythritol acid, pyrrolidone acid and its salts, dihydroxyacetone, erythrulose, glyceraldehyde, tartaraldehyde, clove oil, menthol, camphor, *eucalyptus* oil, eugenol, menthyl lactate, witch hazel distillate, eicosene and vinyl pyrrolidone copolymers, iodopropyl butylcarbamate, a polysaccharide, an essential fatty acid, salicylate, glycyrrhetinic acid, carotenoides, ceramides and pseudo-ceramides, a lipid complex, oils in general of natural origin such as shea butter, shea oil, apricot oil, onagre oil, *prunus* oil, palm oil, monoi oil, HEPES; procysteine; O-octanoyl-6-D-maltose; the disodium salt of methylglycinediacetic acid, steroids such as diosgenin and derivatives of DHEA; DHEA or dehydroepiandrosterone and/or a precursor or chemical or biological derivative, N-ethyloxycarbonyl-4-para-aminophenol, bilberry extracts; phytohormones; extracts of the yeast *Saccharomyces cerevisiae*; extracts of algae; extracts of soyabean, lupin, maize and/or pea; alverine and its salts, in particular alverine citrate, extract of butcher's broom and of horse chestnut, and mixtures thereof, a metallopreoteinase inhibitor.

The compositions of the present invention can comprise one or more particulate materials. Non limiting examples of particulate materials useful in the present invention include colored and uncolored pigments, interference pigments, inorganic powders, organic powders, composite powders, optical brightener particles, and combinations thereof. These particulates can, for instance, be platelet shaped, spherical, elongated or needle-shaped, or irregularly shaped, surface coated or uncoated, porous or non-porous, charged or uncharged, and can be added to the current compositions as a powder or as a pre-dispersion. In one embodiment, particulate materials are present in the composition in levels of from about 0.01% to about 20%, more preferably from about 0.05% to about 10%, still more preferably from about 0.1% to about 5%, by weight of the composition. There are no specific limitations as to the pigment, colorant or filler powders used in the composition.

Particulate materials useful herein can include, but are not limited to, bismuth oxychloride, sericite, mica, mica treated with barium sulfate or other materials, zeolite, kaolin, silica, boron nitride, lauroyl lysine, nylon, polyethylene, talc, styrene, polypropylene, polystyrene, ethylene/acrylic acid copolymer, aluminum oxide, silicone resin, barium sulfate, calcium carbonate, cellulose acetate, PTFE, polymethyl methacrylate, starch, modified starches such as aluminum starch octenyl succinate, silk, glass, and mixtures thereof. Preferred organic powders/fillers include, but are not limited, to polymeric particles chosen from the methylsilsesquioxane resin microspheres such as, for example, those sold by Toshiba silicone under the name Tospearl 145A, microspheres of polymethylmethacrylates such as those sold by Seppic under the name Micropearl M 100, the spherical particles of crosslinked polydimethylsiloxanes, especially such as those sold by Dow Corning Toray Silicone under the name Trefil E 506C or Trefil E 505C, sphericle particles of polyamide and more specifically Nylon 12, especially such as those sold by Atochem under the name Orgasol 2002D Nat C05, polystyerene microspheres such as for example those sold by Dyno Particles under the name Dynospheres, ethylene acrylate copolymer sold by Kobo under the name FloBead EA209, PTFE, polypropylene, aluminium starch ocetenylsuccinate such as those sold by National Starch under the name Dry Flo, microspheres of polyethylene such as those sold by Equistar under the name of Microthene FN510-00, silicone resin, polymethylsilsesquioxane silicone polymer, platelet shaped powder made from L-lauroyl lysine, and mixtures thereof.

Also useful herein are interference pigments. The most common examples of interference pigments are micas layered with about 50-300 nm films of $TiO_2$, $Fe_2O_3$, silica, tin oxide, and/or $Cr_2O_3$. Useful interference pigments are available commercially from a wide variety of suppliers, for example, Rona (Timiron and Dichrona), Presperse (Flonac), Kobo (SK-45-R and SK-45-G), BASF (Lumina) and Eckart (e.g. Prestige Silk Red).

Other pigments useful in the present invention can provide color primarily through selective absorption of specific wavelengths of visible light, and include inorganic pigments, organic pigments and combinations thereof. Examples of such useful inorganic pigments include iron oxides, ferric ammonium ferrocyanide, manganese violet, ultramarine blue, and Chrome oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present invention, for example TiO2, ZnO, or ZrO2, are commercially available from a number of sources. One example of a suitable particulate material contains the material available from U.S. Cosmetics (TRONOX TiO2 series, SAT-T CR837, a rutile TiO2).

The pigments/powders of the current invention can be surface treated to provide added stability of color and/or for ease of formulation. Non-limiting examples of suitable coating materials include silicones, lecithin, amino acids, metal soaps, polyethylene and collagen. These surface treatments may be hydrophobic or hydrophilic, with hydrophobic treatments being preferred.

According to a further embodiment, the compositions of the subject invention may optionally contain a sunscreen active. As used herein, "sunscreen active" includes both sunscreen agents and physical sunblocks. Suitable sunscreen actives may be organic or inorganic.

A wide variety of conventional organic or inorganic sunscreen actives are suitable for use herein. In one embodiment, the composition comprises from about 0.1% to about 20%, more typically from about 0.5% to about 10% by weight of the composition, of the sun screen active. Exact amounts will vary depending upon the sunscreen chosen and the desired Sun Protection Factor (SPF).

As examples of organic screening agents which are active in UV-A and/or UV-B, there may be mentioned in particular those designated below by their CTFA name: para-aminobenzoic acid derivatives: PABA, Ethyl PABA, Ethyl Dihydroxypropyl PABA, Ethylhexyl Dimethyl PABA sold in particular under the name "ESCALOL 507" by ISP, Glyceryl PABA, PEG-25 PABA sold under the name "UVINUL P25" by BASF, salicyclic derivatives: Homosalate sold under the name "EUSOLEX HMS" by RONA/EM INDUSTRIES, Ethylhexyl Salicylate sold under the name "NEO HELIOPAN OS" by HAARMANN and REIMER, Dipropyleneglycol Salicylate sold under the name "DIPSAL" by SCHER, TEA Salicylate, sold under the name "NEO HELIOPAN TS" by HAARMANN and REIMER, dibenzoylmethane derivatives: Butyl Methoxydibenzoylmethane sold in particular under the trademark "PARSOL 1789" by HOFFMANN LA ROCHE, Isopropyl Dibenzolylmethane, cinnamic derivatives: Ethylhexyl Methoxycinnamate sold in particular under the trademark "PARSOL MCX" by HOFFMANN LA ROCHE, Isopropyl Methoxy Cinnamate, Isoamyl Methoxy Cinnamate sold under the trademark "NEO HELIOPAN E 1000" by HAARMANN and REIMER, Cinoxate, DEA Methoxycinnamate, Diisopropyl Methylcinnamate, Glyceryl Ethylhexanoate Dimethoxycinnamate, 3, r-diphenylacrylate derivatives: Octocrylene sold in particular under the trademark "UVINUL N539" by BASF, Etocrylene, sold in particular under the trademark "UVINUL N35" by BASF, benzophenone derivatives: Benzophenone-1 sold under the trademark "UVINUL 400" by BASF, Benzophenone-2 sold under the trademark "UVINUL D50" by BASF, Benzophenone-3 or Oxybenzone, sold under the trademark "UVINUL M40" by BASF, Benzophenone-4 sold under the trademark "UVINUL MS40" by BASF, Benzophenone-5, Benzophenone-6 sold under the trademark "HELISORB 11" by NORQUAY, Benzophenone-8 sold under the trademark "SPECTRA-SORB UV-24" by AMERICAN CYANAMID, Benzophenone-9 sold under the trademark "UVINUL DS-49" by BASF, Benzophenone-12, benzylidene camphor derivatives: 3-Benzylidene Camphor, 4-Methylbenzylidene Camphor sold under the name "EUSOLEX 6300" by MERCK, Benzylidene Camphor Sulphonic Acid, Camphor Benzalkonium Methosulphate, Terephthalylidene Dicamphor Sulphonic Acid, Polyacrylamidomethyl Benzylidene Camphor, phenylbenzimidazole derivatives: Phenylbenzimidazole Sulphonic Acid sold in particular under the trademark "EUSOLEX 232" by MERCK, Benzimidazilate sold under the trademark "NEO HELIOPAN AP" by HAARMANN and REIMER, triazine derivatives: Anisotriazine sold under the trademark "TINOSORB S" by CIBA GEIGY, Ethylhexyl triazones sold in particular under the trademark "UVINUL T150" by BASF, Diethylhexyl Butamido Triazone sold under the trademark "UVASORB HEB" by SIGMA 3V, phenylbenzotriazole derivatives: Drometrizole Trisiloxane sold under the name "SILATRIZOLE" by RHODIA CHIMIE, anthranilic derivatives: Menthyl anthranilate sold under the trademark "NEO HELIOPAN MA" by HAARMANN and REIMER, imidazoline derivatives: Ethylhexyl Dimethoxybenzylidene Dioxoimidazoline Propionate, benzalmalonate derivatives: Polyorganosiloxane with benzalmalonate functional groups sold under the trademark "PARSOL SLX" by HOFFMANN LA ROCHE, and mixtures thereof others: dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); uric and violuric acids; tannic acid and its derivatives (e.g., hexaethylether); (butyl carbotol) (6-propyl piperonyl)ether; hydroquinone;

The organic UV-screening agents which are more particularly preferred are chosen from the following compounds: Ethylhexyl Salicylate, Butyl Methoxydibenzoylmethane, Ethylhexyl Methoxycinnamate, Octocryl ene, Phenylbenzimidazole Sulphonic Acid, Terephthalylidene Dicamphor Sulphonic, Benzophenone-3, Benzophenone-4, Benzophenone-5,4-Methylbenzylidene camphor, Benzimidazilate, Anisotriazine, Ethylhexyl triazone, Diethylhexyl Butamido Triazone, Methylene bis-Benzotriazolyl Tetramethylbutylphenol, Drometrizole Trisiloxane, and mixtures thereof. Also preferred are the compositions described in U.S. Pat. No. 6,190,645 and in particular, sunscreen agents sold under the trademark INCROQUAT-UV-283 manufactured by Croda, Inc.

The inorganic screening agents which may be used in the composition according to the invention are in particular nanopigments (mean size of the primary particles: generally between 5 nm and 100 nm, preferably between 10 nm and 50 nm) of coated or uncoated metal oxides such as for example nanopigments of titanium oxide (amorphous or crystallized in the form of rutile and/or anatase), iron, zinc, zirconium or cerium oxides and mixtures thereof. Coating agents are moreover alumina and/or aluminum stearate. Such nanopigments of metal oxides, coated or uncoated, are in particular described in EP-A-O-518,772 and EP-A-O-518,773.

When used herein, the inorganic sunscreens are present in the amount of from about 0.1% to about 20%, preferably from about 0.5% to about 10%, more preferably from about 1% to about 5%, by weight of the composition.

According to an embodiment, the viscosity of the composition is generally that of a gel. Generally, the viscosity is a minimum of about 1,000, 2,000, 5,000, 10,000, 15,000, preferably about 20,000 to a maximum of about 12,000,000, 2,000,000, or about 600,000 cps. Viscosity is measured by standard techniques such as the use of a Brookfield Viscometer. Those skilled in the art will use the appropriate spindle and speed combination to cover the range of viscosity to be measured. For less viscous samples, Brookfield spindle #5, at 20 rpm and 20° C., is suitable. At high viscosities, a helipath attachment is used with, for example, spindle T-E at 2.5 rpm and 20° C. For example, a preferred range of viscosity of about 500,000 to 1,200,000 cps is measured with a Brookfield Viscometer using a helipath attachment with a T-E spindle at 2.5 rpm and about 20° C.

According to another embodiment, the composition has a pH in a range favorable for maintaining a stable gel composition, while also remaining dermatologically acceptable. In embodiments which comprise a thickener based on acrylic acid polymers, a pH adjusting amount of a basic substance such as sodium hydroxide is present to produce a pH in a range of about 4 to about 7, or 4.5 to 5. This pH adjustment offsets the effects of other acidic ingredients and activates the thickening of the composition provided by acid-functional polymers, such as Carbopol Ultrez 30. Other pH Adjusters that could be included are: Inorganic bases (Ammonium hydroxide, potassium hydroxide, magnesium hydroxide, silver bicarbonate), triethanolamine, citric acid, lactic acid, sodium phosphates (mono, tri).

EXAMPLES

Materials

The test compositions are described in the Table 1, below.

TABLE 1

| Ingredient | Formulations | | |
|---|---|---|---|
| | Example 1 (Test Gel) | Example 2 (Test Gel) | Example 3 (Test Gel) |
| Demineralized Water | 94.86 | 90.36 | 91.38 |
| Carbomer | 0.6 | 0.6 | 0.6 |
| Polyethylene glycol 400 | — | 4 | — |
| Polyethylene glycol 600 | — | 2 | — |
| Trimethylglycine | 1 | — | 2 |
| PEG-14M | 0.1 | 0.1 | 0.1 |
| Propylene Glycol | 0.1 | 0.1 | 0.1 |
| Glycerin | 2 | 2 | 4 |
| PEG 60 Almond Glycerides | — | — | 0.5 |
| Shea Oil | 0.5 | — | 0.5 |
| Fragrance | 0.4 | 0.4 | 0.4 |
| Blend of Sorbitan Caprylate, Propanediol and Benzoic Acid | 0.35 | 0.35 | 0.35 |
| Sodium Hydroxide (50%) | 0.086 | 0.093 | 0.071 |
| Demineralized Water | 89.33 | 90.95 | 90.45 |
| Carbomer | 0.6 | 0.4 | 0.4 |
| Polyethylene glycol 400 | — | 4 | — |
| Polyethylene glycol 600 | — | 2 | — |
| Trimethylglycine | 1 | 2 | 2 |
| PEG-14M | 0.1 | 0.1 | 0.1 |

TABLE 1-continued

| Ingredient | Formulations | | |
|---|---|---|---|
| | Example 1 (Test Gel) | Example 2 (Test Gel) | Example 3 (Test Gel) |
| Propylene Glycol | 0.1 | 0.1 | 0.1 |
| Glycerin | 4 | 4 | 4 |
| PEG 60 Almond Glycerides | — | — | 0.5 |
| Polyglyceryl-3 Laurate | 0.75 | 0.75 | 0.75 |
| PPG-3 Isostearyl Methyl Ether | 0.75 | 0.75 | 0.75 |
| Shea Oil | 0.5 | 0.5 | 0.5 |
| Fragrance | 0.3 | 0.4 | 0.4 |
| Blend of Sorbitan Caprylate, Propanediol and Benzoic Acid | 1.5 | 0.35 | 0.35 |
| Sodium Hydroxide (50%) | 0.073 | 0.1 | 0.1 |

Example 1

Panelists' forearms, were measured for skin hydration using a skin hygrometer, Skicon-200 manufactured by I.B.S Company, Ltd., Hamamatsu, Japan. Skicon-200 measures conductance at a fixed current of 3.5 MHz. The measuring probe (surface 0.28 cm$^2$) consists of two concentric gold-covered electrodes (with respective external diameters of 2 mm and 5 mm). The distance between the inner and the outer electrode is 1 mm. A high frequency current of a few µA flows when the probe is placed on the measurement area. The measurement values are given in micro-siemens units (µs), ranging from 0 to 1999 µs.

A moisturizing lotion and three moisturizing gel formulation products were applied to the forearm in five successive treatment sessions, labeled in FIG. 1 as Treatment 1, Treatment 2, Treatment 3, Treatment 4, and Treatment 5. The samples were measured at intervals after application of each treatment and skin hydration values were recorded as a percentage of the baseline value. FIG. 1 presents a graph of the results of the testing of the data for the three moisturizing gels according to the invention, and an oil-in-water emulsion-based lotion as a comparative example.

The commercially available lotion based on oil-in water emulsion evaluated as the Comparative Example contains the following ingredients, as described on its label: Aqua, Petrolatum, Glycerin, Isopropyl Palmitate, Cetearyl alcohol, Sodium Lactate, Hexyldecanol, Hexyldecyl laurate, PEG-100 Stearate, Glyceryl Stearate, Lactic Acid, Dimethicone, Glyceryl Oleate, Parfum, Sodium Benzoate, Xanthan Gum, Tocopheryl Acetate, Linoleic Acid, Allantoin, Caprylyl Glycol, Linolenic acid, Example 2

Twenty-four female subjects having mild to moderate skin dryness on the lower leg (scored as 1 or 2 on a 4-point dryness scale, as rated visually by a trained observer) were identified for inclusion in a study to assess moisturization provided by topical application of test sample compositions.

The subjects were placed on a daily regimen using a non-moisturizing cleanser for one week prior to testing, and were required to refrain from showering within 12 hours of treatment within the study. The test compositions were the inventive gel composition of Example 1, and two Traditional Oil-in-Water Emulsions, Comparative A and Comparative B.

The test compositions were applied once a day for five (5) days. The skin dryness of the twenty-four subjects was evaluated at three points in time: after the one week pretreatment ("Before"), 1 hour after the first treatment ("1 hour [day] #1), and at various hours after treatment on Day 5 ("x hour [day] #5)", with x indicating 1, 2, 4, 6, 8 hours after treatment on day 5).

Skin dryness was measured in three ways: (1) visual evaluation by a trained grader; (2) corneometer instrument measurement of skin hydration; (3) self-assessment questionnaire (SAQ): skin feels soft, smooth, greasy.

TABLE 2

Skin Dryness, Visual

|  | $T_0$ | $T_{1hour}$ Day#1 | $T_{8hours}$ Day#5 |
|---|---|---|---|
| Example 1 | 1.5 ± 0.4 | 0.8 ± 0.3 | 0.7 ± 0.3 |
| Comparative A | 1.5 ± 0.3 | 0.8 ± 0.3 | 0.9 ± 0.3 |
| Comparative B | 1.5 ± 0.3 | 0.9 ± 0.3 | 0.9 ± 0.3 |
| Untreated Control | 1.5 ± 0.3 | 1.5 ± 0.3 | 1.6 ± 0.3 |

TABLE 3

Skin Hydration

|  | $T_{1hour}$ Day#5 | $T_{2hour}$ Day#5 | $T_{4hours}$ Day#5 | $T_{6hours}$ Day#5 | $T_{8hours}$ Day#5 |
|---|---|---|---|---|---|
| Example 1 | 0.5 ± 0.1 | 0.6 ± 0.2 | 0.6 ± 0.2 | 0.7 ± 0.3 | 0.7 ± 0.3 |
| Comparative A | 0.6 ± 0.2 | 0.6 ± 0.2 | 0.7 ± 0.2 | 0.8 ± 0.3 | 0.9 ± 0.3 |
| Comparative B | 0.7 ± 0.2 | 0.7 ± 0.3 | 0.8 ± 0.3 | 0.9 ± 0.3 | 0.9 ± 0.3 |
| Untreated Control | 1.6 ± 0.4 | 1.6 ± 0.4 | 1.6 ± 0.4 | 1.6 ± 0.4 | 1.6 ± 0.4 |

| Softness | $T_0$ | $T_{1hour}$ Day1 | $T_{8hours}$ Day5 |
|---|---|---|---|
| Example 1 | 0.5 ± 0.7 | 1.8 ± 0.8 | 1.9 ± 0.8 |
| Comparative A | 0.5 ± 0.6 | 2.2 ± 0.8 | 2.2 ± 0.8 |
| Comparative B | 0.5 ± 0.6 | 2.0 ± 0.8 | 1.7 ± 1.1 |
| Untreated Control | 0.5 ± 0.7 | 0.4 ± 0.6 | 0.1 ± 0.4 |

| Smoothness | $T_0$ | $T_{1hour}$ Day1 | $T_{8hours}$ Day5 |
|---|---|---|---|
| Example 1 | 0.5 ± 0.6 | 1.7 ± 0.9 | 2.0 ± 0.9 |
| Comparative A | 0.5 ± 0.7 | 2.1 ± 0.8 | 2.2 ± 0.8 |
| Comparative B | 0.5 ± 0.7 | 2.0 ± 0.9 | 1.7 ± 1.0 |
| Untreated Control | 0.5 ± 0.7 | 0.4 ± 0.6 | 0.1 ± 0.3 |

| Greasiness | $T_0$ | $T_{1hour}$ Day1 | $T_{8hours}$ Day5 |
|---|---|---|---|
| Example 1 | 0 ± 0 | 0.5 ± 0.7 | 0.8 ± 1.1 |
| Comparative A | 0 ± 0 | 1.5 ± 1.0 | 0.7 ± 0.9 |
| Comparative B | 0 ± 0 | 1.0 ± 0.9 | 0.5 ± 0.9 |
| Untreated Control | 0 ± 0 | 0 ± 0 | 0 ± 0 |

Overall Study Results:

Visual Skin Dryness—As shown in Table 2, All compositions demonstrated a significant decrease in dryness from Baseline ($T_0$) and compared to the Untreated Control. The gel of Example 1, however, provided improved softness, smoothness and greasiness over the Comparative Example A and B lotions.

Measured Corneometer Results—As shown in Table 3, all compositions demonstrated a significant increase in moisturization compared to the Untreated Control. The test moisturizing gel, Example 1, demonstrated results similar to, if not better than, the comparative moisturizing lotion.

Self-Assessment Questionnaire—as shown in Tables 4a and 4b, the subjects perceived a significant improvement in 'Softness' and "Smoothness' for all compositions after the first application on day #1, and 8 hours after application on day #5. Table 4c further shows that subjects perceived a significant improvement in 'Greasiness' for all compositions after the first application on day #1 and 8 hours after application on day #5.

What is claimed is:

1. A moisturizing gel composition, consisting of:
   1 wt. % to 12 wt. % of a humectant selected from trimethylglycine, propylene glycol, glycerin and combinations thereof;
   1 wt. % to 6 wt. % of a skin feel agent selected from PEG-14M, polyglyceryl-3-laurate, PPG-3 isostearyl methyl ether, PEG 60 almond glyceride, and combinations thereof;
   0.25 wt. % to 1 wt. % of a skin conditioning agent selected from triterpene esters;
   0.2 wt. % to 2 wt. % of a structure increasing polymer selected from carbomers, acrylate polymers, acrylate copolymers and combinations thereof;
   0.25 wt % to 3 wt % of preservative;
   a pH adjuster;
   a cosmetically acceptable aqueous carrier;
   70 wt. % to 96 wt. % water,
   wherein, the composition has a pH of 4 to 7; and
   wherein the viscosity of the del is 5,000 cps to 300,000 cps, as measured on a Brookfield Viscometer.

2. The composition of claim 1, wherein the humectant is present at 4 wt. % to 12 wt. %.

3. The composition of claim 1, wherein the skin feel agent is present at 1 wt. % to 4 wt. %.

4. The composition of claim 1, wherein the skin conditioning agent is present at 0.4 wt. % to 0.8 wt. %.

5. The composition of claim 1, wherein the structure increasing polymer is present at 0.4 wt. % to 0.8 wt. %.

6. The composition of claim 1, wherein the triterpene ester is selected from rice bran oil, shea butter oil, avocado oil, olive oil, soybean oil, rapeseed oil, mango butter, argan oil, palm oil, red palm oil, coconut oil, palm kernel oil, safflower oil, cocoa butter, almond oil, sunflower oil, peach kernel oil, evening primrose oil, sesame oil, illipe butter, borage oil, cottonseed oil, babassu oil, sal butter, kokum butter, shorea butter, corn oil, corn fiber oil, groundnut oil, flax seed oil, murumuru butter, cupuacu butter, macadamia oil, and combinations thereof.

7. The composition of claim 1, wherein the preservative is a blend of Sorbitan Caprylate, Propanediol and Benzoic Acid.

8. The composition of claim 1, wherein the pH adjuster is sodium hydroxide.

9. A process for preparing a moisturizing gel composition, wherein the process is a cold process, comprising:
   combining ingredients at ambient temperature of from 15° C. to 35° C., without the need of external heating, wherein the ingredients consist of:
   a. 1 wt. % to 12 wt. % of a humectant selected from trimethylglycine, propylene glycol, glycerin and combinations thereof;
   b. 1 wt. % to 6 wt. % of a skin feel agent selected from PEG-14M, polyglyceryl-3-laurate, PPG-3 isostearyl methyl ether, PEG_60 almond glyceride, and combinations thereof;
   c. 0.25 wt. % to 1 wt. % of a skin conditioning agent selected from triterpene esters;

d. 0.2 wt. % to 2 wt. % of a structure increasing polymer selected from carbomers, acrylate polymers, acrylate copolymers and combinations thereof;
e. a cosmetically acceptable carrier;
f. 0.25 wt. % to 3 wt % of preservatives; and
70 wt. % to 96 wt. % water;
blending the ingredients, and; adding a pH adjuster to activate thickening of the composition and provide a pH of 4 to 7, and a viscosity of 5,000 cps to 300,000 cps.

* * * * *

UNITED STATES PATENT AND TRADEMARK OFFICE
CERTIFICATE OF CORRECTION

| | | |
|---|---|---|
| PATENT NO. | : 11,166,885 B2 | Page 1 of 1 |
| APPLICATION NO. | : 16/334490 | |
| DATED | : November 9, 2021 | |
| INVENTOR(S) | : Farrah Syed et al. | |

It is certified that error appears in the above-identified patent and that said Letters Patent is hereby corrected as shown below:

In the Specification

In Column 4, Line 16, delete "tradenarne" and insert -- tradename --, therefor.

Signed and Sealed this
Fourth Day of January, 2022

Drew Hirshfeld
*Performing the Functions and Duties of the
Under Secretary of Commerce for Intellectual Property and
Director of the United States Patent and Trademark Office*